(12) United States Patent
Magers et al.

(10) Patent No.: US 8,323,324 B2
(45) Date of Patent: Dec. 4, 2012

(54) THERAPEUTIC HEATING AND COOLING VIA TEMPERATURE MANAGEMENT OF A COLON-INSERTED DUAL BALLOON

(75) Inventors: Michael Magers, Encinitas, CA (US); Juan C. Lasheras, La Jolla, CA (US)

(73) Assignee: Innercool Therapies, Inc., San Diego, CA (US)

( * ) Notice: Subject to any disclaimer, the term of this patent is extended or adjusted under 35 U.S.C. 154(b) by 1046 days.

(21) Appl. No.: 12/257,295

(22) Filed: Oct. 23, 2008
(Under 37 CFR 1.47)

(65) Prior Publication Data
US 2009/0270955 A1 Oct. 29, 2009

Related U.S. Application Data

(63) Continuation-in-part of application No. 10/832,031, filed on Apr. 26, 2004, now Pat. No. 7,491,223, which is a continuation of application No. 09/881,175, filed on Jun. 14, 2001, now Pat. No. 6,726,708.

(60) Provisional application No. 60/211,406, filed on Jun. 14, 2000.

(51) Int. Cl.
*A61F 7/12* (2006.01)
(52) U.S. Cl. .................................. 607/105; 607/104
(58) Field of Classification Search ............ 607/104–107
See application file for complete search history.

(56) References Cited

U.S. PATENT DOCUMENTS 4,361,107 A * 11/1982 Gereg ........................... 116/266
6,746,465 B2 * 6/2004 Diederich et al. ............ 606/192

* cited by examiner

*Primary Examiner* — Roy Gibson

(57) ABSTRACT

Methods and apparatus are provided for heating or cooling a patient's whole body or a selected portion of a patient's body. In one embodiment, the method begins by inserting a catheter having a dual balloon system into the large intestine of a patient. A heated or chilled liquid is conducted through a supply tube of the catheter and into the inner balloon. The liquid is evacuated from the inner balloon through a return lumen of the catheter. The outer balloon conducts heat transfer between the patient's tissues and the inner balloon, and further provides a degree of safety against rupture of the inner balloon.

25 Claims, 7 Drawing Sheets

THERAPEUTIC HEATING AND COOLING VIA TEMPERATURE MANAGEMENT OF A COLON-INSERTED DUAL BALLOON

STATEMENT OF RELATED APPLICATIONS

This application is a continuation-in-part of U.S. patent application Ser. No. 10/832,031, entitled "THERAPEUTIC HEATING AND COOLING VIA TEMPERATURE MANAGEMENT OF A COLON-INSERTED BALLOON", filed on Apr. 26, 2004 now U.S. Pat. No. 7,491,223, which is a continuation of U.S. patent application Ser. No. 09/881,175, entitled "THERAPEUTIC HEATING AND COOLING VIA TEMPERATURE MANAGEMENT OF A COLON-INSERTED BALLOON", filed on Jun. 14, 2001, now U.S. Pat. No. 6,726,708, which claims the benefit of U.S. Provisional Patent Appl. Ser. No. 60/211,406, entitled "THERAPEUTIC HEATING AND COOLING VIA TEMPERATURE MANAGEMENT OF A COLON-INSERTED BALLOON," filed on Jun. 14, 2000. All of these prior applications are hereby incorporated by reference in their entirety.

BACKGROUND OF THE INVENTION

I. Field of the Invention

The present invention relates generally to the modification and control of the temperature of the body. More particularly, the invention relates to a method for controlling body temperature by heat transfer using a balloon.

II. Description of the Related Art

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Patients may require rewarming or cooling for a variety of reasons, including, for example, treatment of a malignant hypothermia or hyperthermia crisis as well as induction of therapeutic hypothermia for a number of reasons, particularly tissue preservation for indications including heart maladies, stroke, trauma, and neurosurgery.

Catheters have been developed which are inserted into the bloodstream of the patient in order to induce total body hypothermia. For example, U.S. Pat. No. 3,425,419 to Dato describes a method and apparatus of lowering and raising the temperature of the human body. The Dato invention is directed towards a method of inducing moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel.

Other less cumbersome catheters have been developed to provide cooling intravascularly. For example, a heat transfer element such as disclosed in U.S. Pat. No. 6,096,068, incorporated herein by reference in its entirety, may be placed in the feeding artery of an organ to absorb or deliver the heat from or to the blood flowing into the organ. The transfer of heat may cause either a cooling or a heating of the selected organ. The heat transfer element is small enough to fit within the feeding artery while still allowing a sufficient blood flow to reach the organ in order to avoid ischemic organ damage. By placing the heat transfer element within the feeding artery of an organ, the temperature of the organ can be controlled with less of an effect on the temperature of the remaining parts of the body. A similar heat transfer device, which is employed for whole body cooling and which may be disposed in the venous vasculature, is disclosed in U.S. Pat. No. 6,843,800, also incorporated by reference in its entirety.

While the previously mentioned techniques provide significant thermal control, they require the insertion of a catheter into the vascular system to induce heat transfer between the catheter and the blood stream. This is a relatively invasive procedure, which has an associated level of risk.

Accordingly, it would be desirable to provide an effective, less invasive method and apparatus for heating or cooling all or part of a patient's body. It would also be desirable to provide an effective, less invasive method and apparatus for heating or cooling all or part of a patient's body that could be employed in emergency situations, such as on an ambulance.

SUMMARY OF THE INVENTION

The present invention provides methods for regulating the temperature of a patient's whole body or one or more selected organs thereof, and devices for use therein. Devices of the invention have a high degree of flexibility and are collapsible, thereby affording an easy insertion procedure, and further allow a high surface area to increase heat transfer.

In one aspect, the invention provides methods and apparatus for heating or cooling at least a selected portion of a patient's body through the transfer of heat to or from the at least a selected portion in an efficient manner. In one embodiment, the method begins by inserting a balloon catheter through the anus into the colon of the patient. The system includes a supply lumen and an at least partially inflatable return lumen. The return lumen is coupled to the supply lumen so as to transfer working fluid between the two. A heated or chilled fluid is conducted through the supply lumen of the catheter and into the balloon. The fluid is evacuated from the balloon through the return lumen of the catheter. Heat transfer occurs between the working fluid and the tissue of the colon.

Variations of the system may include one or more of the following. The supply lumen and the return lumen may be made of a flexible material such as latex rubber or other plastics. The radii of the supply and return lumens may decrease in a distal direction such that the supply and return lumens are tapered when inflated. A wire may be disposed in the supply or return lumens to provide shape and strength when deflated. The thickness of the return lumen, when inflated, may be less than about ½ mil. The length of the supply lumen may be between about 5 and 150 or more centimeters.

The system may further include a coaxial supply catheter having an inner catheter lumen coupled to the supply lumen and a working fluid supply configured to dispense the working fluid and having an output coupled to the inner catheter lumen. The working fluid supply may be configured to produce a pressurized working fluid at a temperature of between about −3° C. and 50° C. Higher or lower temperatures may be employed if desired.

In another aspect, the invention is directed to methods and apparatus of changing the temperature of a body by heat transfer. In one embodiment, the method includes inserting an inflatable heat transfer element into the colon of a patient and inflating the same by delivering a working fluid to its interior.

The temperature of the working fluid is generally different from that of the colon tissue. The flexible, conductive heat transfer element preferably absorbs more than about 500 watts of heat.

The circulating may further include passing the working fluid in through a supply lumen and out through a return, coaxial lumen. The working fluid may be a liquid at or well below its boiling point, and furthermore may be aqueous.

Advantages of the invention may include one or more of the following. The heat transfer element successfully achieves patient cooling or heating. The heat transfer element has a small diameter when deflated, large diameter when inflated, high flexibility, and enhanced heat transfer rate through the significant surface area of the heat transfer element. The process is relatively non-invasive. In addition, rapid cooling or heating to a precise temperature may be achieved. Further, treatment of a patient is not cumbersome and the patient may easily receive continued care during the heat transfer process. The device and method may be easily combined with other devices and techniques to provide aggressive multiple therapies. The device may employ saline, which is very commonly-available, as a working fluid. The device has a very high surface area, particularly as the length may be on the order of a meter and the diameter on the order of 0.1 meters. Use of the device may be performed without sedation of the patient. The power transferred during cooling may be as high as 600 to 1000 watts. Other advantages will become clear from the description below, including the figures and claims, as well as from the above.

BRIEF DESCRIPTION OF THE DRAWINGS

The novel features, objects, and advantages of the invention will become more apparent from the detailed description set forth below when taken in conjunction with the drawings in which like reference characters identify corresponding elements throughout.

Like reference numerals indicate like elements throughout.

DETAILED DESCRIPTION OF THE INVENTION

Figure 1:
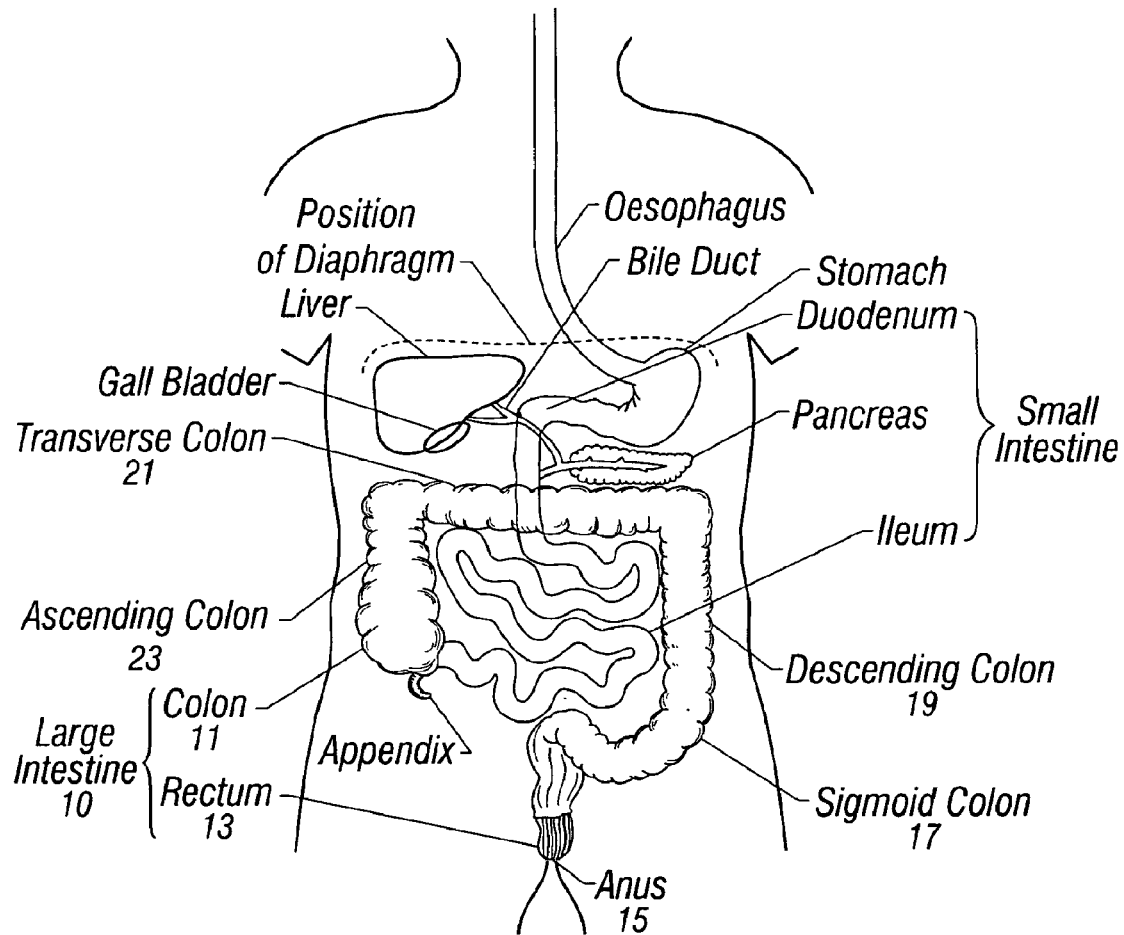
FIGS. 1 and 2 illustrate schematic diagrams of the digestive tract, FIG. 2 being an expanded view.
Figure 2:
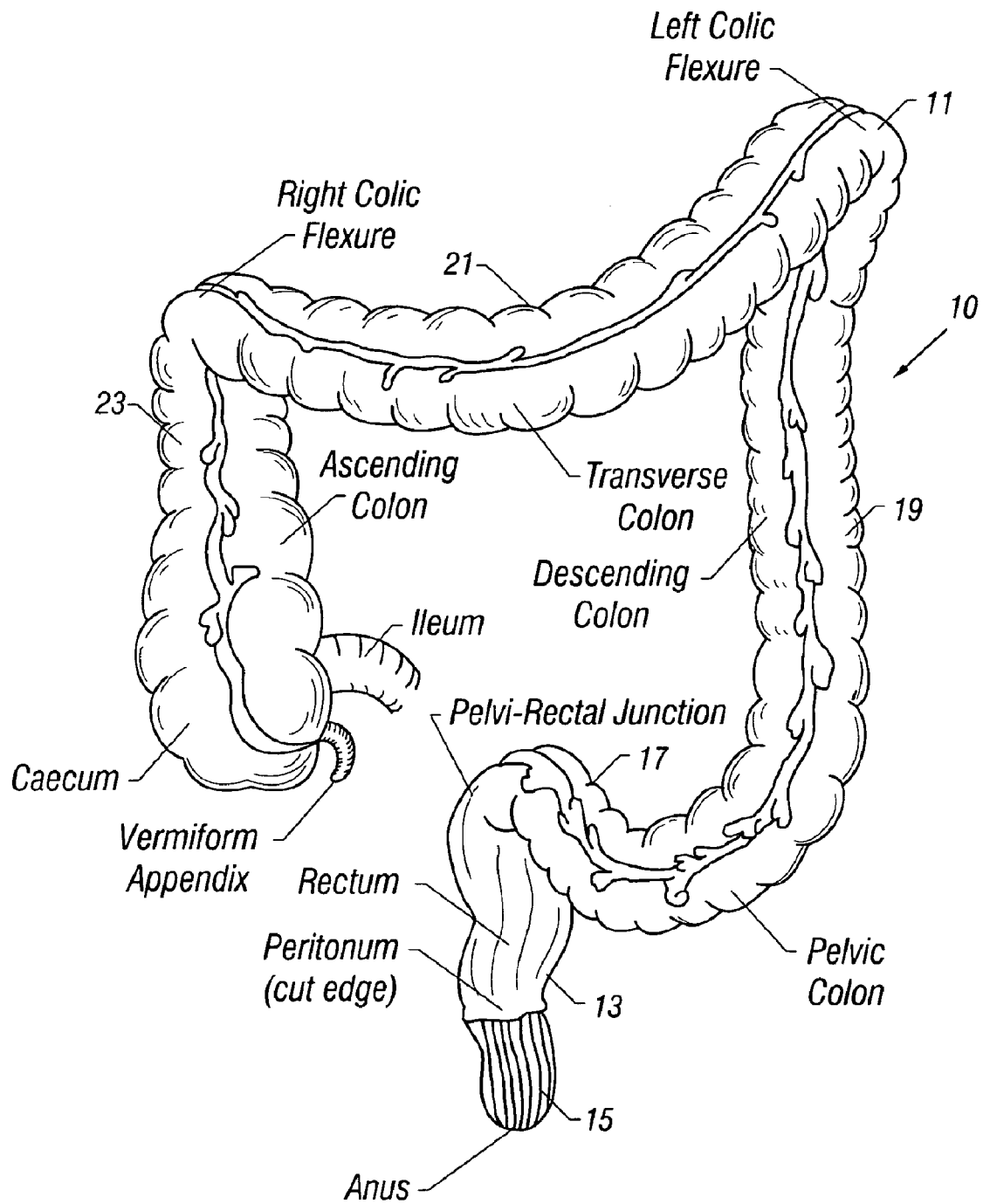
Figure 3:
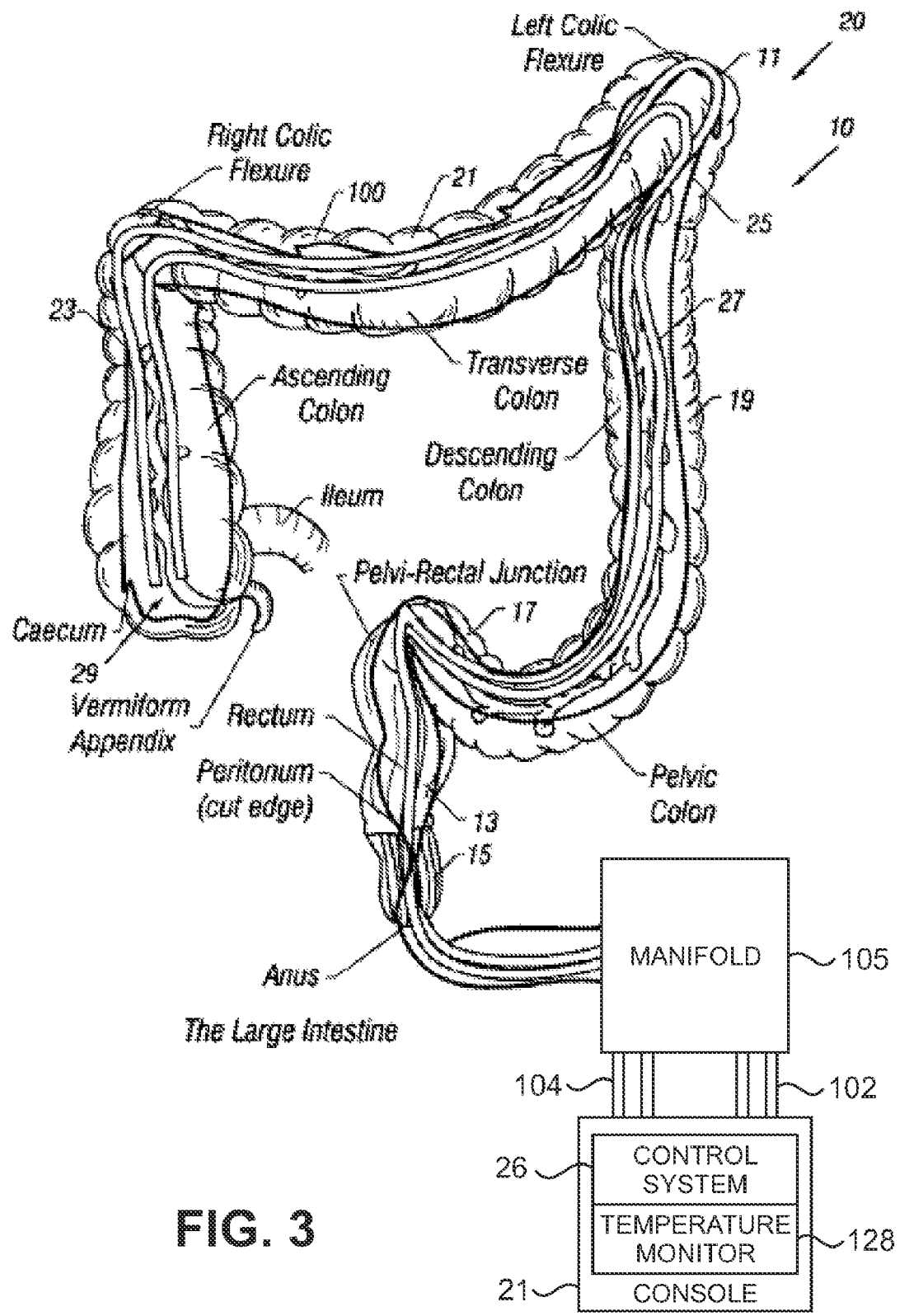
FIGS. 3 and 4 illustrate a schematic diagrams of a device according to an embodiment of the invention, FIG. 4 being a simplified view of FIG. 3.
Figure 4:
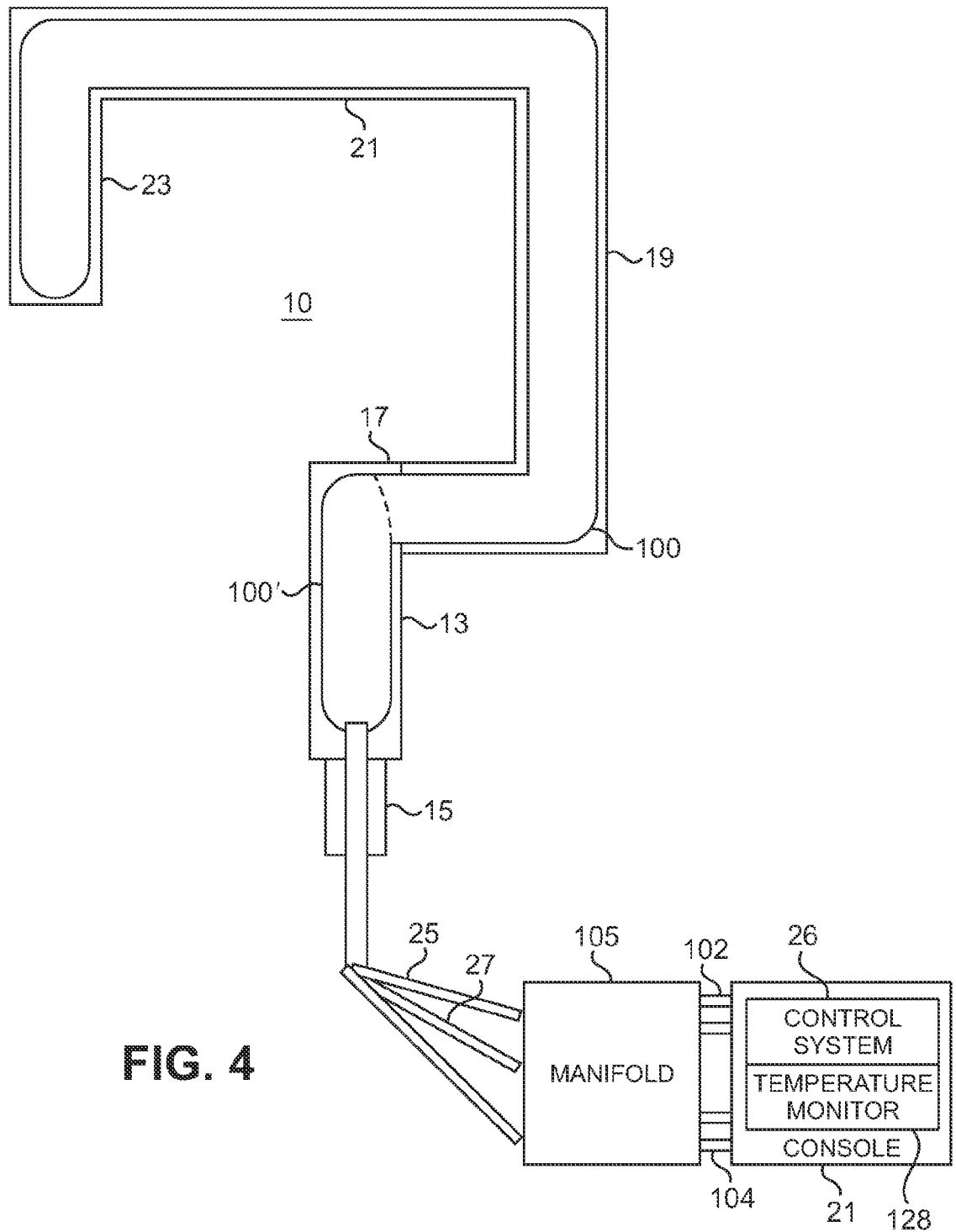

The present invention provides relatively non-intrusive methods and apparatus for heating or cooling all or part of a patient's body. FIGS. 3-4 illustrate a heat transfer fluid circulated through a balloon that has been placed in one or more portions of the large intestine. As shown in FIGS. 1-4, the large intestine 10 comprises the colon 11 and the rectum 13. The final stage in the digestive process is passage through the anus 15. The colon 11 has four parts: the ascending colon 23, the transverse colon 21, the descending colon 19, and the sigmoid colon 17. Various other components are also shown in FIG. 1. FIG. 2 shows an enlarged view of the large intestine 10 and colon 11.

Heat transfer via the colon 11 is advantageous because the colon 11 is located in the abdominal cavity, is surrounded by a variety of organs, and in addition the tissues of the colon walls may be highly perfused with blood. Further, the abdominal cavity volume includes a substantial portion of the high blood flow vessels the aorta and the inferior vena cava. The working fluid absorbs heat from or delivers heat through the wall of the colon 11 and into the abdominal cavity and the arterial and venous vessels populating this area, thereby regulating the temperature of a patient's whole body or one or more selected organs. With regard to regulating the temperature of a patient's whole body, cooling of the internal organs and a considerable amount of blood can be accomplished without the invasive step of inserting a catheter directly into the vascular system. With regard to regulating the temperature of one or more selected organs, the cooling (or heating) balloon may influence the temperature of a number of organs and other body parts in close proximity to the disposed balloon, for example, the bladder and associated nerves and neurovascular bundles, the urethra, the uterus, the vagina, the prostate, the anus, and the rectum. As described herein, the use of an analogous balloon catheter disposed within the stomach can also provide temperature management of a patient's whole body or one or more selected organs in close proximity to the disposed balloon in the stomach (for example, the liver and the lungs).

The mechanism of heat transfer into and out of the catheter is via conduction. Once the tissue of the colon has a modified temperature, the mechanism of heat transfer may be via convection through the blood as well as by conduction through the tissue.

As shown in FIGS. 3-4, within the large intestine, the catheter is disposed within the rectum and may additionally be disposed at various lengths within the colon depending on the desired amount of patient cooling or warming or on the selected organs to be cooled or warmed. Thus, depending on the particular temperature regulation needed, the disposed catheter may have its distal end located within the rectum (as depicted by 100" with dashed line in FIG. 4) or with increasing catheter lengths, located in the sigmoid colon 17, in the descending colon 19, in the transverse colon 21 or in the ascending colon 23 (as depicted as 100 in FIGS. 3 and 4). As used herein, catheter 100 refers to any catheter of the invention for placement within the patient's body (including exemplary catheters 100 and 100' depicted in FIGS. 3 and 4 and those depicted in FIGS. 6A, 6B and 7).

FIG. 3 shows one embodiment of the colon thermal control system constructed in accordance with the present invention. The system includes a catheter 100, a control system 26, and a circulation set (not shown) partially housed by a console 21. The control system 26 may be equipped with an output display and input keys to facilitate user interaction. The core body temperature may be determined by a temperature monitor 128, which may be an esophageal monitor, a tympanic monitor, or any other type of temperature monitor as is known in the art with which core body temperature may be monitored. The complexity of the console 21 depends on the application to which the same is put. For example, for a rewarming application, the console 21 may be a Mallinkrodt Blood and Fluid Warmer, as manufactured by Mallinkrodt Medical of St. Louis, Mo. In the same way, for certain applications, such as for rewarming or maintaining normothermia during a surgery or other procedure, the heat exchanger used within the control system may a resistive heat exchanger or thermoelectric heat exchanger.

The catheter 100, which may employ a design similar to that of a large balloon catheter, for example, is configured for insertion into the colon. The proximal end of the catheter 100 includes a manifold 105 having an inlet port 102 and an outlet port 104 on its proximal end. The supply lumen 27 and the return lumen 25 are connected to a port located on the distal end of the manifold 105. At the catheter's distal end the supply and return lumens are fluidically coupled via an orifice. The catheter may have an inflated diameter of, e.g., 1-10 cm or another size as dictated by the requirements of the user.

The catheter 100 may be made of a very soft material so as to minimize tissue damage of the colon and other organs upon insertion. The same may be coated with various materials to minimize deleterious coating of undesired biological materials on the tip during or after insertion.

The supply and return lumens may be formed from a pair of concentric flexible tubes so that the supply lumen may be concentrically located within the annular return lumen. Of course, the same may also be non-coaxial as dictated by the requirements of the user. As shown in FIG. 3, when the catheter 100 is properly inserted into the colon to provide heat transfer throughout the length of the colon, its distal end may be located in the ascending colon 23. Fluid is conducted into the balloon, i.e., into the inflatable return lumen 25, from the supply lumen 27 via an orifice 29.

As in a conventional Foley catheter for the urethra, the catheter 100 may include an additional anchoring balloon (not shown) near its proximal end to prevent its expulsion from the colon. The anchoring balloon may also serve the purpose of anchoring the catheter against movement caused by a pulsating working fluid supply, as may be the case if certain types of pumps are employed to drive the working fluid. The anchoring balloon may be inflated by a single inflation lumen, a dual inflation lumen, or other such lumen as is known.

The circulation set and console may include any of the features of such systems described in co-pending applications: Ser. No. 60/247,203, filed Nov. 7, 2000, entitled "Improved Circulation Set for Temperature Controlled Catheter and Method of Using Same", and Ser. No. 09/827,010, filed Apr. 5, 2001, entitled "Method and Apparatus for Regulating Patient Temperature by Irrigating the Bladder with a Fluid", both of which are incorporated herein by reference in their entirety. These applications disclose one or more of the following: a fluid reservoir, a pump, a filter, a heat exchanger, a temperature and pressure sensor assembly, a supply line, and a return line. The supply line and return line may be comprised of one or more pieces of tubing, connectors, etc. joining the aforementioned components of the circulation set. The circulation set supplies, filters, circulates, and monitors the temperature and pressure of the heat transfer fluid for the catheter 100. The pressure inside the balloon is preferably not higher than about 10 psi, and may be about 0 to 3 psi.

In one embodiment, the fluid reservoir is a modified IV bag made of PVC filled with saline. Considering the heat transfer expected, the flow rate of the saline may be about 10 to 100 cc/sec, or even higher. The temperature of the saline may vary such that in a cooling mode, the saline is maintained between about 0° C. and 5° C., whereas in heating the same is maintained between about 40° C. and 42° C. Other fluids may also be used according to the requirements of the user.

The fluid reservoir is used to prime the lines of the circulation set and the lumens of the catheter 100. For example, the system may be primed with 0.9% saline, and then the pump speed adjusted appropriately.

The heat exchanger, which is used to heat or chill the fluid supplied to the catheter, may be any of a variety of conventionally designed heat exchangers. As noted above, the heat exchanger may employ a resistive heater, a microwave heater, a thermoelectric device, a closed-circuit temperature control system, etc.

The temperature and pressure sensor assembly may include alarms that shut down the system if a dangerous situation arises. For example, a maximum safe temperature of working fluid may be about 50° C. If this temperature were exceeded, the system may be designed to shut itself down or even turn itself off. Alternatively, a high temperature may be allowed, but only for a short predetermined period of time, insufficient to cause tissue damage.

A control system may be provided to accept a temperature feedback signal and to control the temperature of the working fluid thereby. Of course, it is noted that the location of the catheter 100, in the abdominal cavity, may have an associated time delay with respect to the patient temperature due to the slow mechanism of heat transfer (e.g., by conduction) through the colon walls. Such a time lag may be expected to be about 10 to 20 minutes.

The fluid may be provided to the supply lumen in a continuous, constant flow or as a pulsed flow of fluid. The pulsed flow may be a flow that is either intermittently interrupted or simply reduced in rate on an intermittent basis. For example, the flow rate may be pulsed at a frequency of every few minutes. The present invention also contemplates more complex flow rate patterns such as periodic and aperiodic oscillatory patterns.

As the insertion of a rectal-type catheter is generally uncomplicated, and can be performed by nurses or emergency personnel, the system may be implemented on an emergency vehicle such as an ambulance. For such systems, a compressed gas system may be used to cool a circulating fluid. It is again noted that in heating embodiments a simple resistive heater may be employed.

Figure 5A:
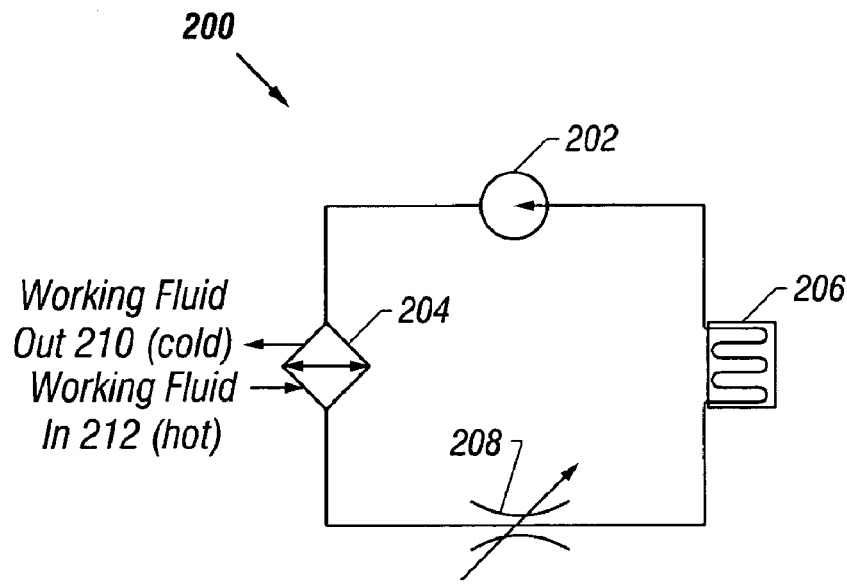
FIG. 5A illustrates a prior art heat exchange system.

Prior chiller units employing a closed cycle evaporative gas system were complicated, expensive, and difficult to simplify and miniaturize for use in a portable transportable system. Further, they required significant electrical power to operate. For example, referring to FIG. 5A, a prior art refrigeration system 200 is shown. Such a system is exceedingly well-known, and includes a pump 202, a heat exchanger 204, a restriction valve 208, and an apparatus 206 to exhaust heat to a temperature bath. In this system, as is known, a liquid-to-gas heat exchanger transfers heat from the working fluid to the cold side of an evaporative chiller.

Figure 5B:
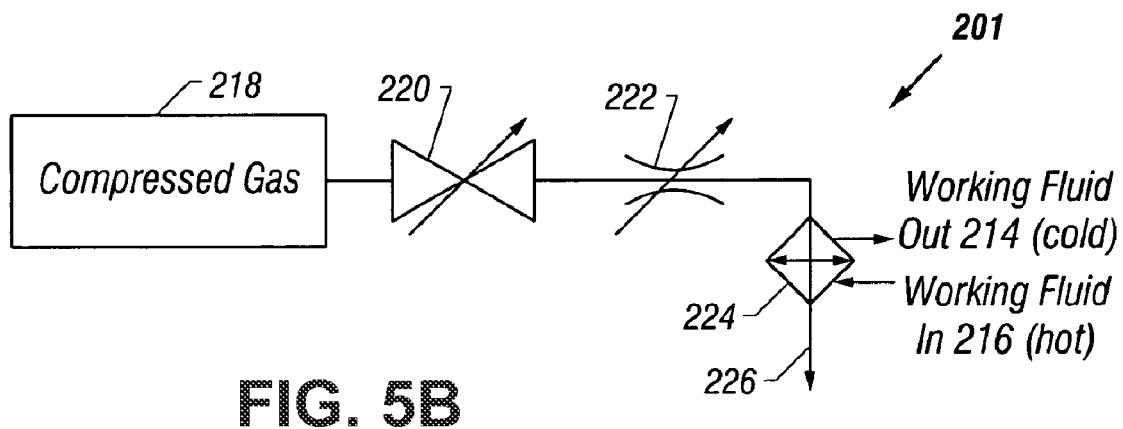
FIG. 5B illustrates a heat exchange system constructed in accordance with an embodiment of the invention.

A system 201 is shown in FIG. 5B. In this figure, a source of compressed gas 218 is valvably coupled via valve 220 to an optional restriction valve 222 to a heat exchanger 224. A working fluid output for, e.g., a cold working fluid, is labeled by outlet 214. A working fluid input for, e.g., a higher-temperature working fluid, is labeled by inlet 216. An exhaust to the environment is shown as exhaust 226.

In system 201, a compressed gas from source 218 is expanded adiabatically through a valve. The expansion results in a reduced-temperature gas that absorbs heat from the working fluid in the liquid-to-gas heat exchanger 224. The heated, expanded gas is then discarded to the environment via exhaust 226. An additional temperature reduction in the expanded gas may be achieved by the phase change from the storage pressure to the expanded pressure.

Gases which may be useful in systems employing adiabatic expansion include nitrogen, carbon dioxide, etc. Gases which may be useful in systems employing adiabatic expansion with a phase change include nitrous oxide.

Figure 6A:
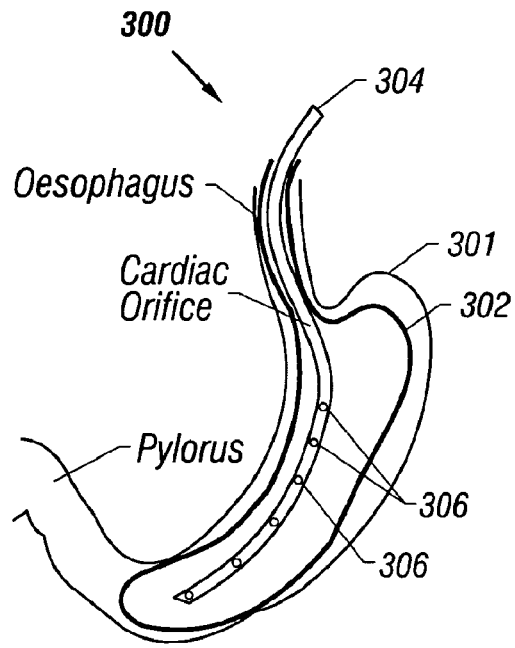
FIGS. 6A and 6B illustrate embodiments of an alternative embodiment of the invention in use within the stomach, showing both deflated and inflated states.
Figure 6B:
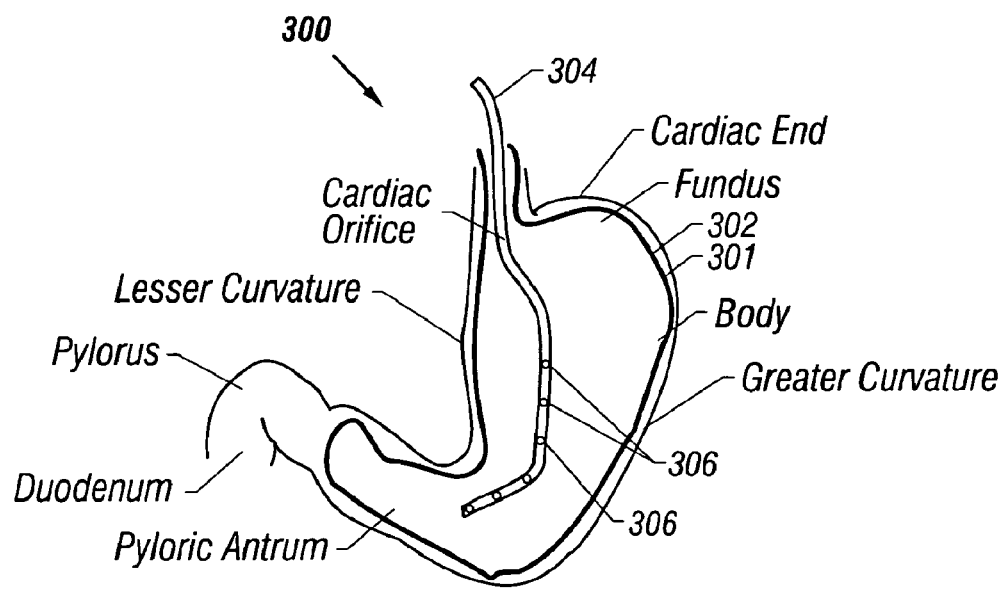

Referring to FIGS. 6A and 6B, it should also be clear to one of ordinary skill in the art given the teaching herein that an analogous balloon 300 may be located in the stomach 301 to cool or heat that organ and thus the vasculature surrounding the stomach, leading to temperature management of all or a portion of the patient. A plurality of longitudinally-spaced working fluid exits 306 may be disposed along a supply lumen 304 that is placed within a return lumen 302 having the approximate shape of a stomach 301. In such a way, the return lumen 302 when inflated takes the approximate shape of the stomach to enhance heat transfer. The temperature and pressure requirements of this embodiment may be approximately the same as that in the colon embodiment, although this embodiment would be inserted through the esophagus. This embodiment may have the further advantage of being in close proximity to the liver, lungs, as well as other major arteries and veins. Thus, convection can rapidly become a major component of heat transfer and it is expected that power of up to or in excess of 1000 watts can be transferred.

As described, systems are provided which provide independent balloons for heat exchange and for expansion into the rectal cavity. For example, by using two balloons, an inner balloon and an outer balloon, the working fluid volume required to be employed is lessened. The system includes a supply lumen and a return lumen to circulate liquid into and out of the inner balloon. Two balloons also provide for a redundant safety balloon in the event the inner balloon was to rupture due to overpressurization and/or a blocked circulating return tube. The systems may accommodate a variety of sizes of patients. In use, the method begins by inserting the dual-balloon catheter through the anus into the rectum of the patient (the balloon may either fill the rectum or a portion thereof, or may extend somewhat into the colon). A heated or chilled liquid is conducted through the supply lumen of the catheter and into the inner balloon. The outer balloon, with the stationary liquid supply, conducts heat between the inner balloon and the patient. The liquid is evacuated from the inner balloon through the return lumen of the catheter. Heat transfer occurs between the working fluid, the liquid in the outer balloon, and the patient's tissues.

Figure 7:
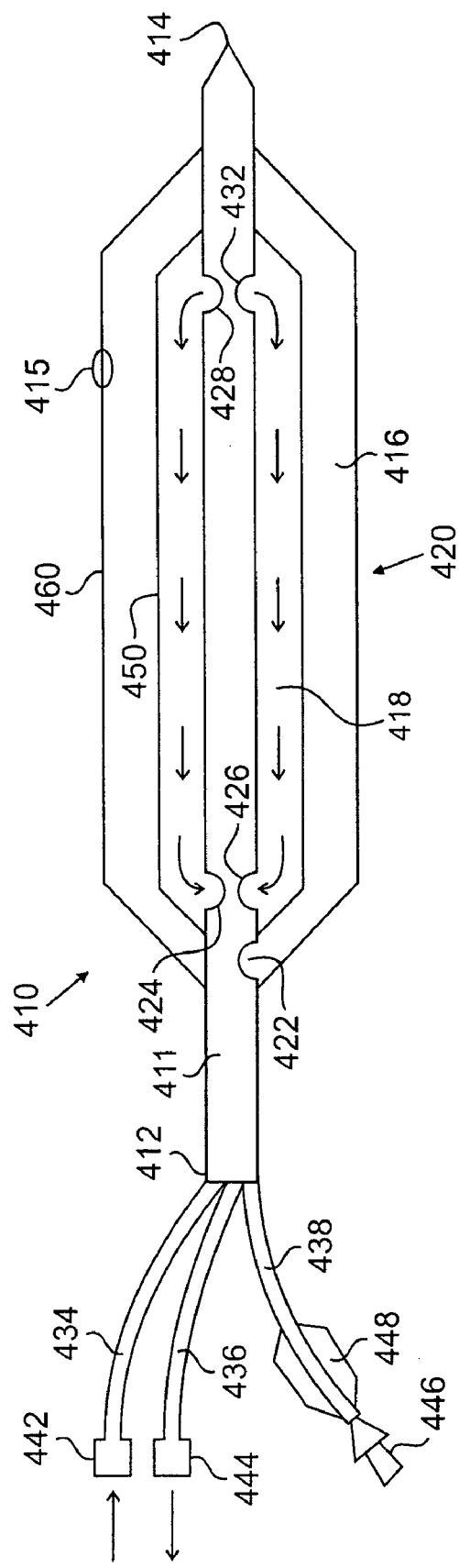
FIG. 7 illustrates a schematic depiction of a dual-balloon device that may be employed in certain embodiments of the invention.

Referring to FIG. 7, an embodiment of a dual-balloon system 410 is illustrated that may be employed in the system. The dual balloon system has a distal end 414, a proximal end 412, and a balloon 420 generally adjacent the distal end 414. The balloon 420 is a dual balloon, and generally includes an inner balloon 450 enclosing an inner lumen 418 and an outer balloon 460 enclosing an outer lumen 416. The inner balloon 450 and outer balloon 460 are shown concentric, but they need not be. In generally, the outer balloon will surround the inner balloon, but the same may be off-center or in other arrangements as well.

The balloons are disposed around a central catheter shaft 411. The central catheter shaft 411 may be equipped with multiple lumens for delivering liquids to the inner balloon 450, the outer balloon 460, or both. In particular, the central catheter shaft 411 includes a lumen that is fed from a supply tube 438 which is closed by a valve 446. The supply tube 438 ends at an inlet 422 which allows the supply tube 438 to deliver liquid to the outer balloon 460. More than one inlet may be provided; however, only one is required. The central catheter shaft 411 also includes one or more lumens that are fed from a circulating supply tube 434 which attaches via connector 442 to a circulation set from a refrigeration and rewarming console. The central catheter shaft 411 further includes one or more lumens that extend from a circulating return tube 436 which attaches via connector 444 to the circulation set from a refrigeration and rewarming console. The circulating supply tube 434 ends at one or more inlet 428 and 432 which allow the circulating supply tube 434 to deliver liquid to the inner balloon 450. The circulating return tube 436 extends from one or more inlets 424 and 426 which allow the circulating return tube 436 to return liquid from the inner balloon 450. More than two inlets and outlets may be provided.

As shown in FIG. 7, an over-inflation indicator 448 may be provided to ensure that safe levels of inflation are employed for the outer balloon 460. The over-inflation indicator 448 may be a balloon that when inflated indicates that the outer balloon is full.

A temperature sensor 415, e.g., a thermistor, may be disposed on the outer surface of the outer balloon in order to measure the rectal wall temperature. A temperature signal from the temperature sensor may then provide a feedback signal to the source of working fluid and its control system. The feedback signal can then provide a way to control the temperature of the balloon-rectum interface. A physician may select a desired patient temperature, and the console may then control to this temperature.

The embodiment of FIG. 7 allows independent pressurization of the outer balloon, which is then used for filling the rectal cavity and allowing a high-conductivity cooling pathway. The inner balloon, with its circulating liquid, allows for convective removal of removed heat and thus advantageous heat transfer.

In use, high-pressure liquid, e.g., saline, is caused to flow in the circulating supply tube 434, in the central shaft, and then into the inner balloon 450. This circulating liquid flows out of the inner balloon and out of the circulating return tube 436. The liquid generally enters in a high-pressure state and exits in a lower-pressure state. The inlets 428 and 432 may be shaped and configured so as to provide a 'jet' effect for the circulating liquid, enhancing mixing of the liquid within the inner balloon. The outer balloon 460 is filled with another biocompatible liquid, such as saline, and may be filled with, e.g., 200-300 cc's of saline. The distal tip 414 may be tapered, such as in a dilator, for ease of insertion.

Various other elements may be sized as follows, although it should be noted that these dimensions are purely exemplary. The central catheter shaft 411 may have an outer diameter of 0.5", and may be constructed of Tygon®. The outer balloon 460 may have an outer diameter of 3", and be 6" long. The inner balloon may have an outer diameter of 2", and may be 5.5" long.

While the invention herein disclosed is capable of obtaining the objects hereinbefore stated, it is to be understood that this disclosure is merely illustrative of the presently preferred embodiments of the invention and that no limitations are intended other than as described in the appended claims. For example, the invention can be used in a wide variety of settings, e.g., in the applications of general surgery, and in particular lengthy surgeries, orthopedic and back surgery, liver transplants, etc. Further, suction may be implemented on the return lumen in order to maintain even lower pressures inside the balloon, particularly when the flow rate of working fluid is increased to 10-200 cc/s. A guide wire may be used to place the catheter 100 in the desired location. While the colon embodiment shown spans the ascending, transverse, and descending colons for maximum power transferred, lower power requirements may be met by placing the catheter in less than the entire colon.

The invention claimed is:

1. A method for heating or cooling a patient's body, comprising:
   inserting a catheter into at least a portion of the rectum, the catheter including a dual balloon, the dual balloon including an outer balloon and an inner balloon;
   inflating the outer balloon with a liquid;

conducting a heated or chilled liquid through a supply tube into the inner balloon; and a supply lumen of the catheter; and evacuating the liquid from the inner balloon through a return tube.

2. The method of claim 1, further comprising monitoring the temperature of the liquid in either the liquid conducted into the supply tube or the liquid flowing through the return tube.

3. The method of claim 1, further comprising controlling the temperature of the heated or chilled liquid based on a measured patient temperature.

4. The method of claim 3, wherein the measured patient temperature is a patient rectal wall temperature.

5. A method for heating or cooling a patient's body, said method comprising:
    installing a catheter with an inner balloon and an outer balloon into at least a portion of the rectum of a patient;
    inflating the outer balloon with a liquid;
    irrigating the inner balloon with a heated or chilled liquid;
    controlling at least one measurable parameter of the liquid irrigating the inner balloon; and
    evacuating the liquid from the inner balloon.

6. The method of claim 5, wherein the at least one measurable parameter is selected from the group consisting of the flow rate of the liquid, the pressure of the liquid flowing into or out of the inner balloon, and the temperature of the liquid flowing into or out of the inner balloon.

7. The method of claim 5, wherein the controlling is at least in part based on a measured patient temperature.

8. The method of claim 7, wherein the measured patient temperature is a patient rectal wall temperature.

9. An apparatus for heating or cooling at least a selected portion of a body, comprising:
    a catheter having a proximal end and a distal end, the catheter configured to be disposed in at least a portion of the rectum of a patient, wherein heat transfer to and from the catheter controls at least in part a patient temperature;
    a dual balloon system disposed near the distal end of the catheter, the dual balloon system including an inner balloon and an outer balloon; and
    an inflation indicator configured to indicate a level of inflation of the outer balloon;
    wherein the inner balloon is coupled to at least one inlet and at least one outlet such that heated or chilled liquid may be circulated through the inner balloon, and wherein the outer balloon is configured to be inflated by a further liquid, and
    wherein the at least one inlet of the inner balloon is shaped to provide a jet effect for enhancing mixing of the heated or chilled liquid circulated through the inner balloon.

10. The apparatus of claim 9, further comprising a temperature-controlled source for circulating the heated or chilled liquid, coupled to the catheter, for delivering the heated or chilled liquid to and from the inner balloon, and a control system for controlling at least one measurable parameter of the heated or chilled liquid circulating to the inner balloon.

11. The apparatus of claim 10, further comprising a monitoring device for monitoring the at least one measurable parameter, wherein the at least one measurable parameter is selected from the group consisting of: the flow rate of the heated or chilled liquid, pressure of the heated or chilled liquid flowing into and out of the inner balloon, a patient temperature, and temperature of the heated or chilled liquid flowing into or out of the inner balloon.

12. The apparatus of claim 11, wherein the monitoring device monitors a patient rectal wall temperature.

13. The apparatus of claim 10, wherein the control system includes at least one input key and an output display.

14. The apparatus of claim 13, wherein the control system further comprises a resistive heater or a thermoelectric temperature controller.

15. The apparatus of claim 10, wherein the source of circulating liquid includes a disposable intravenous bag in thermal communication with a heat exchanger.

16. The apparatus of claim 10, wherein the temperature-controlled source is configured such that the heated or chilled liquid is circulated through the inner balloon at a flow rate of between 10 and 100 cc/sec.

17. The apparatus of claim 9, wherein the liquid is saline.

18. The apparatus of claim 9, wherein a diameter of the dual balloon system, when inflated, is between 1 and 10 cm.

19. The apparatus of claim 9, wherein at least one of the inner balloon and the outer balloon includes a biocompatible coating.

20. The apparatus of claim 9, wherein the inlet and the outlet are concentric.

21. The apparatus of claim 9, wherein the inlet and the outlet are side-by-side.

22. The apparatus of claim 9, further comprising an anchoring balloon coupled to the dual balloon system.

23. The apparatus of claim 9, wherein a pressure inside the dual balloon system is less than 10 psi.

24. The apparatus of claim 23, wherein a pressure inside the dual balloon system is less than 3 psi.

25. The apparatus of claim 9, wherein the inflation indicator comprises a further balloon located on a tube connected to the outer balloon for supplying the further liquid, and wherein the at least one inlet of the inner balloon is located at a distal end of the inner balloon away from the inflation indicator and near the distal end of the catheter, and the at least one outlet of the inner balloon is located at a proximal end of the inner balloon near the inflation indicator.

* * * * *